United States Patent [19]

Prier

[11] Patent Number: 4,528,364

[45] Date of Patent: Jul. 9, 1985

[54] REMOVAL OF ALKALINE CATALYSTS FROM POLYETHER POLYOLS AND POLYALKYLENE CARBONATE POLYOLS

[75] Inventor: Donald G. Prier, Baton Rouge, La.

[73] Assignee: The Dow Chemical Company, Midland, Mich.

[21] Appl. No.: 601,877

[22] Filed: Apr. 19, 1984

[51] Int. Cl.$^3$ ............................................. C07C 41/34
[52] U.S. Cl. .................................... 528/370; 260/463; 528/371; 528/405; 528/482; 528/493; 568/620; 568/621
[58] Field of Search ............... 528/370, 371, 405, 482, 528/493; 260/463; 568/620, 621

[56] References Cited

U.S. PATENT DOCUMENTS

| | | | |
|---|---|---|---|
| 3,028,433 | 4/1962 | Leis et al. | 260/615 |
| 3,374,275 | 3/1968 | Dickey | 260/611.5 |
| 3,528,920 | 9/1970 | Niizeki et al. | 252/73 |
| 3,689,462 | 9/1972 | Maximovich | 528/730 |
| 3,951,888 | 4/1976 | Isayama et al. | 526/49 |
| 4,029,879 | 6/1977 | Muzzio | 536/4 |
| 4,110,268 | 8/1978 | Longley et al. | 521/177 |
| 4,111,865 | 9/1978 | Seefried et al. | 521/137 |
| 4,129,718 | 12/1978 | Muzzio | 536/4 |
| 4,137,396 | 1/1979 | Louvar et al. | 536/4 |
| 4,137,398 | 1/1979 | Muzzio | 536/4 |
| 4,287,078 | 9/1981 | Langdon et al. | 252/76 |
| 4,306,943 | 12/1981 | Mori et al. | 203/29 |
| 4,355,188 | 10/1982 | Herold et al. | 528/620 |
| 4,482,750 | 11/1984 | Hetzel et al. | 528/623 |

Primary Examiner—Maurice J. Welsh
Attorney, Agent, or Firm—Norman L. Sims

[57] ABSTRACT

This invention is a method of removing alkaline catalysts from polyether polyols and polyalkylene carbonate polyols which comprises (a) dissolving a polyether polyol or a polyalkylene carbonate polyol in a polar aprotic solvent;

(b) contacting the polyether polyol or polyalkylene carbonate polyol solution with a sufficient amount of an adsorbent which adsorbs alkaline catalysts to adsorb the alkaline catalysts, at a temperature of between about −30° C. and 110° C. under conditions such that the adsorbent adsorbs the alkaline catalysts; and (c) physically separating the adsorbent from the polyol solution.

11 Claims, No Drawings

REMOVAL OF ALKALINE CATALYSTS FROM POLYETHER POLYOLS AND POLYALKYLENE CARBONATE POLYOLS

BACKGROUND OF THE INVENTION

The invention relates to the purification of polyether polyols and polyalkylene carbonate polyols. More specifically, the invention relates to the removal of alkaline catalysts from polyether polyols and polyalkylene carbonate polyols.

Polyether polyols are conventionally produced by the addition-polymerization reaction of an alkylene oxide with an organic compound having at least one active hydrogen atom in the presence of an alkaline catalyst. Polyalkylene carbonate polyols are conventionally produced by the addition-polymerization reaction of an alkylene carbonate, or alkylene oxide and $CO_2$, with an organic compound having at least one active hydrogen atom in the presence of an alkaline catalyst. The resulting reaction mixtures, therefore necessarily contain substantial amounts of these alkaline catalysts. The presence of the alkaline catalysts remaining in the polyether polyols or the polyalkylene carbonate polyols adversely affect the performance thereof in their intended uses such as raw materials for the production of polyurethanes, hydraulic liquids, cosmetics, surfactants, synthetic lubricants and the like.

There are several known methods for the removal of these alkaline catalysts from the polyether polyols or the polyalkylene carbonate polyols. Present commercial practices for the removal of these impurities can involve neutralization of the alkaline catalysts with acids forming insoluble salts and removal of these salts by filtration. Centrifugation, employing mixtures of polyol, water and solvent, can also be employed for the removal of residual catalysts.

The crude polyols without prior neutralization of the catalyst can be treated with a synthetic type adsorbent followed by filtration of the polyol. Present commercial practice involves mixing the polyol and adsorbent with an amount of water ranging from 0.05 to 5.0 percent. Often the polyol quality suffers because of the great risk of oxidizing the polyols due to repeated interruption in the filtration process necessitating a break in the filter press. This attendant exposure to air causes the production of off-grade polyol by increasing undesirable acidity.

A number of patents disclose the use of various acidic materials for the neutralization of the alkaline catalyst followed by filtration of the precipitated salts. Among these are U.S. Pat. Nos. 3,833,669; 3,053,903; 2,983,763; 2,448,664; and 3,016,404. U.S. Pat. No. 3,528,920 discloses the use of synthetic magnesium silicate as an adsorbent for the removal of the catalysts from the various glycol ethers. However, this patent also discloses that the undesirable alkaline catalyst is first neutralized with acid prior to filtration.

The present processes known for removal of alkaline catalysts from polyether polyols and polyalkylene carbonate polyols have several attendant disadvantages. In many of the processes, water is present during the catalyst removal. This results in undesirable and unwanted hydrolysis of the polyols. Further, several of these processes require relatively high temperatures in order to purify the products.

What is needed is a process for the removal of alkaline catalysts from polyether polyols and polyalkylene carbonate polyols in which water is not present and which is carried out at reasonably low temperatures.

SUMMARY OF THE INVENTION

This invention is a method of removing alkaline catalysts from polyether polyols and polyalkylene carbonate polyols which comprises (a) dissolving a polyether polyol or a polyalkylene carbonate polyol in an aprotic solvent;

(b) contacting the polyether polyol or polyalkylene carbonate polyol solution with a sufficient amount of an adsorbent which adsorbs alkaline catalysts to adsorb the alkaline catalysts, at a temperature of between about $-30°$ C. and $110°$ C. under conditions such that the adsorbent adsorbs the alkaline catalysts; and (c) physically separating the adsorbent from the polyol solution.

This process is advantageous as there is no water present to hydrolyze either the polyether polyol or polyalkylene carbonate polyol. Furthermore, this process takes place at reasonably low temperatures.

DETAILED DESCRIPTION OF THE INVENTION

Polyalkylene carbonate polyols useful in this invention are prepared by the condensation of an alkylene carbonate; carbon dioxide and an alkylene oxide; or mixtures of an alkylene carbonate, an alkylene oxide and/or $CO_2$; with an organic compound containing one or more active hydrogen atoms in the presence of an alkaline catalyst or metal salt of an alkaline compound. Examples of these polyalkylene carbonate polyols and methods for preparation of these polyols are contained in Maximovich, U.S. Pat. No. 3,896,090; Maximovich, U.S. Pat. No. 3,689,462; Springmann, U.S. Pat. No. 3,313,782; Stevens, U.S. Pat. No. 3,248,416; Stevens, U.S. Pat. No. 3,248,415; and Stevens, U.S. Pat. No. 3,248,414; all incorporated herein by reference in all relevant portions.

Examples of polyalkylene carbonate polyols for which this invention is useful include polyalkylene carbonate polyols which correspond to formula I

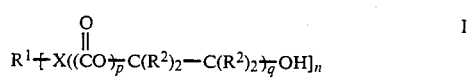

and polyalkylene carbonate block copolymers which correspond to the formula

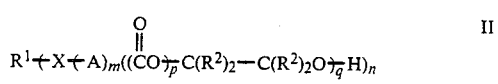

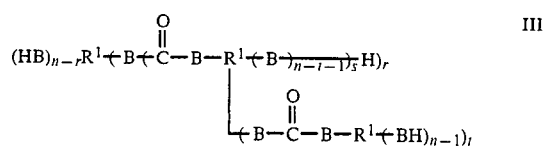

wherein

A is an alkylene ether, amide, amine, aromatic carbonate, ester, imide, sulfide, sulfone or saccharide monomer unit;

B is

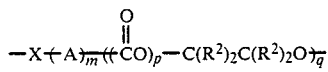

with the proviso that X is always bonded to $R^1$;

$R^1$ is separately in each occurrence an n valent hydrocarbon radical or hydrocarbyloxy hydrocarbon radical;

$R^2$ is separately in each occurrence hydrogen, halogen, a nitro group, a cyano group, a $C_{1-20}$ hydrocarbyl group or a $C_{1-20}$ hydrocarbyl group substituted with one or more of the following: a halo, cyano, nitro, thioalkyl, tert-amino, alkoxy, aryloxy, aralkoxy, carbonyldioxyalkyl, carbonyldioxyaryl, carbonyl dioxyaralkyl, alkoxycarbonyl, aryloxycarbonyl, aralkoxycarbonyl, alkylcarbonyl, arylcarbonyl, aralkylcarbonyl, alkylsulfinyl, arylsulfinyl, aralkylsulfinyl, alkylsulfonyl, arylsulfonyl, or aralkylsulfonyl group;

X is S, O, NH,

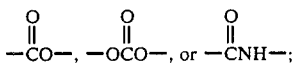

m is separately in each occurrence an integer of from 1 to 200;

n is separately in each occurrence an integer of from 1 to 25;

p is separately in each occurrence 0 or 1;

q is separately in each occurrence an integer of 1 or greater;

r is separately in each occurrence an integer of from 1 to 25;

s is separately in each occurrence an integer of from 1 to 20; and t is separately in each occurrence an integer of from 0 to 24.

In one preferred embodiment, the preferred monomer unit is an alkylene ether unit which is derived from an alkylene oxide. In this preferred embodiment, the polyalkylene carbonate block copolymers correspond to the formulas

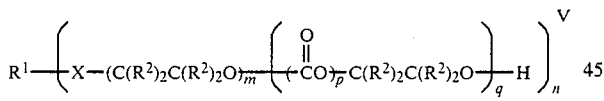

or

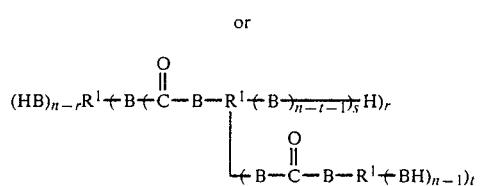

wherein
B is

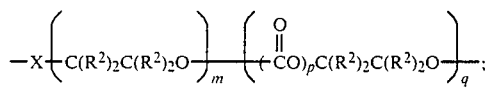

with the proviso that X is always bonded to $R^1$ wherein $R^1$, $R^2$, m, n, p, q, r, s and t are as described above.

The polyalkylene carbonate block copolymers useful in this invention are prepared in two stages. First, the polyalkylene ether, polyamide, aromatic polycarbonate, polyester, polyimide, polysulfide, polysulfone or polysaccharide block is prepared (hereinafter referred to as first stage product). This block is prepared by reacting a suitable organic compound containing active hydrogen atoms with a sufficient amount of a reactant which provides between about 1 and 200 of the units described above per reactive hydrogen-containing moiety on the initiator, preferably between 1 and 75, and more preferably between about 3 and 50, that is m is preferably between about 1 and 75 and more preferably between 3 and 50. These polymerization reactions are well-known in the art. Such polymerization reactions are described in Kirk-Othmer, *Encyclopedia of Chemical Technology*, 3rd Ed., Vol. 18, (relevant portions incorporated herein by reference), for polyamides see pages 328 et seq.; for polyimides see pages 704 et seq.; for polycarbonates see pages 479 et seq.; for polyesters see pages 549 et seq.; for polyethers see pages 594 et seq.; for polysulfides see pages 814 et seq.; for polysulfones see pages 832 et seq. This first stage product has terminal functional groups which contain reactive hydrogens wherein the number of such terminal functional groups is equal to the number of functional groups containing reactive hydrogens on the initiator. Thereafter this product is reacted with alkylene carbonate, alkylene oxide and $CO_2$, alkylene carbonate and alkylene oxide or alkylene carbonate, alkylene oxide or $CO_2$ in a manner such that a polyether polycarbonate block is formed.

The polyether polyols are generally prepared by the condensation of an epoxide with an organic compound containing one or more active hydrogen atoms wherein the condensation takes place in the presence of an alkaline catalyst. The polyether polyols herein include those corresponding to formula VI $$R^1-X-C(R^2)_2-C(R^2)_2-O-_mH)_n \qquad \text{VI}$$

wherein $R^1$, X, m and n are as defined above. Preferably, m is between about 1 and 75 inclusive, more preferably between about 3 and 50 inclusive. Examples of such polyols include those described in Muzzio, U.S. Pat. No. 4,137,398 (incorporated herein by reference).

Alkylene carbonates useful in the reaction are those which will react with the reactive hydrogen-containing functional groups. Desirable alkylene carbonates are those corresponding to formula VII

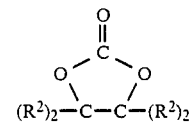

wherein $R^2$ is separately in each occurrence hydrogen, halogen, a nitro group, a cyano group or a monovalent hydrocarbon $C_{1-20}$ or a monovalent hydrocarbon $C_{1-20}$ substituted with one or more of the following: a halo, cyano, nitro, thioalkyl, tert-amino, alkoxy, aryloxy, aralkoxy, carbonyldioxyalkyl, carbonyldioxyaryl, carbonyldioxyaralkyl, alkoxycarbonyl, aryloxycarbonyl, aralkoxycarbonyl, alkylcarbonyl, arylcarbonyl, aralkylcarbonyl, alkylsulfinyl, arylcarbonyl, aralkylcarbonyl, alkylsulfinyl, arylsulfinyl, aralkylsulfinyl, alkylsulfonyl, arylsulfonyl, or aralkylsulfonyl group.

$R^2$ is preferably hydrogen, or a monovalent $C_{1-20}$ alkane, $C_{1-20}$ haloalkane, $C_{1-20}$ alkene or benzene radical. $R^2$ is more preferably hydrogen, or a monovalent $C_{1-3}$ alkane, $C_{2-3}$ alkene or benzene radical. $R^2$ is most preferably hydrogen, or a monovalent methane or ethane.

Examples of desirable alkylene carbonates include ethylene carbonate, propylene carbonate, butylene carbonate, vinylene carbonate and phenylene carbonate. More preferred alkylene carbonates include ethylene and propylene carbonate.

Epoxides useful in this invention are those which will react with the functional group on an organic compound wherein the functional group contains an active hydrogen so as to add an ether unit to the organic compound.

Desirable epoxides include those corresponding to formula VIII

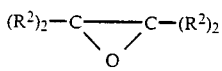   VIII wherein $R^2$ is defined above.

Among desirable epoxides are the alkylene oxides, for instance ethylene oxide, propylene oxide, butylene oxide; epihalohydrins, such as epibromohydrin and epichlorohydrin; styrene oxide, vinylene oxide, cyclohexene oxide; cyclopentene oxide, cycloheptene oxide, 2,3-epoxy propylphenyl ether and tert-butyl glycidyl ether. Among preferred epoxides are ethylene oxide, propylene oxide, epichlorohydrin, epibromohydrin, styrene oxide and vinylene oxide.

The organic compound containing active hydrogen atoms is a hydrocarbon or hydrocarbyloxy hydrocarbon containing between 1 and 25 functional groups containing a reactive hydrogen. Among the desirable hydrocarbon compounds are those which correspond to formula IX

   IX wherein $R^1$ is separately in each occurrence an n valent hydrocarbon or hydrocarbyloxy hydrocarbon radical;

X is separately in each occurrence S, O, NH,

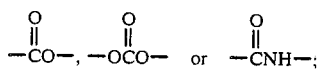

n is an integer of from 1 to 25, inclusive.

A functional group containing a reactive hydrogen means herein any moiety which contains a hydrogen atom which will readily liberate the hydrogen atom and react with one of the units described above. More specifically, reactive hydrogen means herein a hydrogen linked directly to an oxygen, nitrogen or sulfur atom, such as is found in a hydroxy, non-tertiary amine, amide, mercapto or carboxyl group. Hydrocarbyloxy hydrocarbon refers herein to a hydrocarbon radical containing one or more oxy or ether linkages.

$R^1$ is preferably an n valent aliphatic or cycloaliphatic radical. $R^1$ is more preferably an n valent alkane or cycloalkane, and most preferably an n valent $C_{1-10}$ alkane. X is preferably O, S or NH.

The organic compounds containing active hydrogen atoms of this invention contain one or more of the following functional groups, hydroxyls, amines, mercaptans, carboxyls, sulfones, amides, imides, or carbonates.

Among desirable active hydrogen-containing organic compounds are polyols such as aliphatic polyols, cycloaliphatic polyols, aromatic polyols and polyols which further contain oxy or ether groups; polyamines; polymercaptans; polyamides; polycarboxylic acids; alkylolamines and organic compounds which contain three or more of the above-described functional groups containing reactive hydrogens. The preferred classes are the polyols, polyamines and polymercaptans. Examples of active hydrogen-containing compounds include those described in the U.S. patents incorporated by reference hereinbefore.

In the organic compound with a functional group containing an active hydrogen atom described by formula IX, n is preferably between about 1 to 10 inclusive, and most preferably between about 1 to 5.

Catalysts used in the preparation of polyether polyols include alkali metal hydroxides, alkaline earth metal hydroxides, alkali metal carbonates, alkaline earth metal carbonates, ammonium hydroxide and ammonium carbonate.

Suitable catalysts for the reaction of an active hydrogen-containing organic compound and an alkylene carbonate, alkylene oxide and carbon monoxide, or alkylene carbonate in admixture with an alkylene oxide and/or carbon dioxide include ester exchange catalysts. Among suitable catalysts are such metals as lithium, sodium, potassium, rubidium, cesium, magnesium, calcium, strontium, barium, zinc, aluminum, titanium, cobalt, germanium, tin, lead, antimony, arsenic and cerium as well as the alkoxides thereof. Examples of other suitable catalysts are alkali metal carbonates, alkaline earth metal carbonates, ammonium carbonates, alkali metal borates, alkaline earth metal borates, ammonium borates, hydrocarbyloxy titanates, zinc borate, lead borate, zinc oxide, lead silicate, lead arsenate, litharge, lead carbonate, antimony trioxide, germanium dioxide, cerium trioxide and aluminum esopropoxide. Examples of other suitable catalysts include salts of organic acids of magnesium, calcium, cerium, barium, zinc and titanium, alkali metal stannates, alkaline metal stannates and ammonium stannates.

Examples of borate catalysts include sodium metaborate, sodium meta-borate tetrahydrate, sodium metaborate, dihydrate, sodium pentaborate pentahydrate, sodium tetraborate decahydrate, sodium tetraborate pentahydrate, diammonium tetraborate tetrahydrate, ammonium hydrogen tetraborate tetrahydrate, lithium ortho-dihydroborate, lithium meta-borate, lithium tetraborate, lithium pentaborate pentahydrate, potassium meta-borate, potassium tetraborate tetrahydrate, potassium tetraborate pentahydrate, potassium pentaborate tetrahydrate, magnesium meta-borate trihydrate, magnesium diborate, magnesium ortho-borate, calcium meta-borate, calcium tetraborate and strontium tetraborate tetrahydrate. Examples of stannate catalysts include sodium stannate trihydrate, potassium stannate trihydrate, potassium stannate monohydrate, barium stannate trihydrate, magnesium stannate trihydrate and the like.

Preferred catalysts are the alkali metal carbonates, alkaline earth metal carbonates, ammonium carbonates, alkali metal stannates, alkaline earth metal stannates, alkali metal borates, alkaline earth metal borates and ammonium borates. More preferred catalysts are alkali metal carbonates, alkali metal borates and alkali metal stannates. Most preferred catalysts are potassium carbonate, sodium meta-borate and sodium stannate.

For the purposes of this invention, the polyalkylene carbonate polyols are preferred over the polyether polyols.

The alkaline catalysts which are removed by the process of this invention are those which are described hereinbefore, specifically in reference to the catalysts used in the preparation of the polyether polyols and the polyalkylene carbonate polyols.

The choice of solvent is critical to this invention, as by choice of the solvent the polyols can be dissolved in a medium wherein the alkaline catalysts can be adsorbed by the adsorbents without any adverse consequences to the polyol. Generally, aprotic solvents are useful in this process. Preferred solvents are ketones, halogenated aliphatic hydrocarbons, halogenated aromatic hydrocarbons, nitroalkanes, nitrobenzenes, aliphatic nitriles, cyclic amines, alkyl esters, cyclic alkylene carbonates, dialkyl carbonates, alkyl ethers of alkylene glycols, sulfoxides, carbon disulfide, aliphatic ethers, alicyclic ethers, aldehydes, and amides. More preferred solvents are the polar aprotic solvents. Even more preferred solvents include the ketones, ethers, and aldehydes. The most preferred solvents are the ketones.

Examples of suitable ethers are diethylether, dimethylether, and the like. Examples of useful ketones include methylethyl ketone, diethyl ketone, acetone, and the like. Examples of cyclic ethers include tetrahydrofuran and the like. Examples of aldehydes include acetaldehyde, benzaldehyde, and the like.

Examples of halogenated aliphatic hydrocarbons include carbon tetrachloride, chloroform, methylene chloride, methyl chloride, chloroethane, dichloroethane, chloropropane, trichloroethane, and dibromoethane. Examples of halogenated aromatic hydrocarbons include bromobenzenes, chlorobenzenes and iodobenzenes. Examples of nitroalkanes include nitromethane and nitroethane. Examples of aliphatic nitriles include cyanomethane and cyanoethane. Examples of alkyl esters include ethyl formate, ethyl acetate and methyl acetate. Examples of dialkyl carbonates include dimethyl carbonate, diethyl carbonate, dipropyl carbonate and dibutyl carbonate.

Adsorbents useful in this process include those which adsorb alkaline catalysts at temperatures in the range of −30° C. to 110° C. Preferred adsorbents are aluminum and alkaline earth metal silicates. More preferred adsorbents are the alkaline earth metal adsorbents, with magnesium silicate being most preferred.

The preferred magnesium silicate adsorbents may be prepared by the reaction of a magnesium salt such as magnesium sulfate with sodium silicate. The resulting products can have particle sizes ranging from 5 to 500 microns with an average particle size of about 100 to 200 microns. Examples of these adsorbents are sold under the trademarks of "BRIGHTSORB" by Philadelphia Quartz Corporation, and "MAGNASOL" by Reagent Chemicals.

In the process of this invention, the polyether polyol or polyalkylene carbonate polyol is dissolved in one of the solvents described hereinbefore. The concentration of the polyether polyol or the polyalkylene carbonate polyol in the solvent is preferably between about 5 and 95 percent by weight, more preferably between about 15 to 30 percent by weight, and most preferably between about 20 and 25 percent by weight.

This solution is contacted with one of the adsorbents described hereinbefore wherein a sufficient amount of adsorbent to adsorb the alkaline catalyst is used. The concentration of the adsorbent in the solution is preferably an amount such that between 0.01 and 25 percent by weight, based upon the polyol, of adsorbent is present. More preferably between about 5 and 10 percent by weight of the adsorbent is present in the solution. In general, this contacting is done with agitation, such as stirring, so as to allow better contact between the adsorbent and the solution.

It is preferable to run this process in an inert atmosphere, such as in the presence of nitrogen or argon. The presence of oxygen may have deleterious effects upon the polyether polyol or the polyalkylene carbonate polyol.

This contacting takes place for a period of between about 5 minutes and 20 hours, preferably between about 1 and 2 hours.

Contacting is generally done at a temperature of between about −30° C. and 110° C., preferably a temperature of between about 0° C. and 40° C., more preferably between about 10° C. and 30° C., with between about 20° C. and 25° C. being most preferred.

Thereafter the adsorbent and the polyol solution are physically separated. This physical separation can be done by any method known in the art, for example, by filtration.

The polyol can be recovered by stripping off the solvent and drying if there is any water present. Although water is not added, the water may be present as an impurity in the solvent, the adsorbent, or may be picked up from the atmosphere where the process is not done under an inert atmosphere.

In one embodiment, after the polyether polyol or the polyalkylene carbonate polyol is dissolved in a suitable solvent and before the adsorbent is added, the reaction solution can be allowed to stand for a period of time to allow any catalyst that may precipitate to precipitate. Preferably any precipitated catalyst can be separated from the solution before contacting with the adsorbent. This can be done by filtration or decantation. Generally, between 5 minutes and 2 hours are suitable times for any catalyst which may precipitate to do so.

In another embodiment of this invention wherein a ketone is the solvent and the polyol has a relatively high molecular weight, the catalyst precipitates from the solution without the need to use an adsorbent. In this embodiment, the polyol molecular weight is preferably greater than about 1000, and more preferably greater than 1500.

SPECIFIC EMBODIMENTS

The following examples are included for illustrative purposes only, and do not limit the scope of the invention or the claims. Unless otherwise specified, all parts and percentages herein are by weight.

EXAMPLE 1

Into a 500-ml Erlenmeyer flask is placed 80.3 g of polyol reaction mixture, which is the reaction product of 1 mole of glycerol and 10 moles of ethylene carbonate using a 0.10 percent $Na_2SnO_3$ catalyst at room temperature (approx. 23° C.). To the polyol mixture is added 390 ml of acetone to produce a 25 percent solution of the polyol in acetone. The low molecular weight polyol is dissolved in acetone producing a clear solution. To the solution is added 4.0 g of magnesium silicate (5 g of adsorbent/100 g of polyol). The mixture is stirred for 1 hour at room temperature. The solids are filtered out through a coarse, fritted glass filter containing 1 g of Celite ®. The acetone is removed on a rotary evaporator at 70° C. in about 30 minutes. The product is dried by bubbling nitrogen through it at 110° C. for 1 hour. The cleaned up product exhibits a Controlled Polymerization Rate (CPR, measure of residual base contained in the product) of 5.0.

EXAMPLES 2-4

Example 1 is repeated using 2.0, 1.0 and 0.5 g of magnesium silicate per 100 g of the polyol. The results of Examples 2-4 are provided in Table I along with the results of Example 1.

TABLE I

| Example | g silicate/100 g polyol | CPR Value |
| --- | --- | --- |
| 1 | 5.0 | 5.0 |
| 2 | 2.0 | 14.5 |
| 3 | 1.0 | 125.0 |
| 4 | 0.5 | Too high to measure |

What is claimed is:

1. A method of removing alkaline catalysts from polyether polyols and polyalkylene carbonate polyols which comprises
   (a) dissolving a polyether polyol or a polyalkylene carbonate polyol in a polar aprotic solvent;
   (b) contacting the polyether polyol or polyalkylene carbonate polyol solution with a sufficient amount of an adsorbent which adsorbs alkaline catalysts to adsorb the alkaline catalysts, at a temperature of between about −30° C. and 110° C. under conditions such that the adsorbent adsorbs the alkaline catalysts; and
   (c) physically separating the adsorbent from the polyol solution.
2. The process of claim 1 wherein the adsorbent is an aluminum or alkaline earth metal silicate.
3. The process of claim 2 wherein the adsorbent is a magnesium silicate.
4. The process of claim 3 wherein the polyol is a polyalkylene carbonate polyol.
5. The process of claim 4 wherein the solvent is a ketone, an ether, a cyclic ether, an aldehyde or an amide.
6. The process of claim 5 wherein the solvent is a ketone.
7. The process of claim 6 wherein the contacting temperature is between about 0° C. and 40° C.
8. The process of claim 7 wherein the contacting temperature is between about 10° C. and 30° C.
9. The process of claim 8 wherein the polyol is contacted with between about 0.01 and 25 percent by weight of the polyol, of adsorbent.
10. A method of removing alkaline catalysts from polyether polyols and polyalkylene carbonate polyols which comprises
    (a) dissolving between about 5 and 95 percent by weight of a polyether polyol or a polyalkylene carbonate polyol in a polar aprotic solvent;
    (b) allowing the solution to stand for a period sufficient for a portion of the alkaline catalyst to precipitate;
    (c) contacting the polyether polyol or polyalkylene carbonate polyol solution with between about 0.01 and 25.0 weight percent, based on the polyether polyol or polyalkylene carbonate polyol, of an adsorbent which adsorbs alkaline catalysts, at a temperature of between about −30° C. and 110° C. under conditions such that the adsorbent adsorbs the remaining alkaline catalysts; and
    (d) physically separating the adsorbent from the polyol solution.
11. A method of removing alkaline catalyst from polyether polyols and polyalkylene carbonate polyols which comprises
    (a) dissolving between about 5 and 95 percent by weight of a polyether polyol or a polyalkylene carbonate polyol, with a molecular weight of greater than about 1000, in a ketone solvent;
    (b) allowing the solution to stand for a period sufficient for the alkaline catalyst to precipitate; and
    (c) physically separating the alkaline catalysts from the polyol solution.

* * * * *